United States Patent [19]

Lawrence et al.

[11] 4,365,970
[45] Dec. 28, 1982

[54] SPECIMEN TEST SLIDE AND METHOD FOR TESTING OCCULT BLOOD

[75] Inventors: Paul J. Lawrence, Campbell; Charles W. Townsley, San Jose, both of Calif.

[73] Assignee: SmithKline Instruments, Inc., Sunnyvale, Calif.

[21] Appl. No.: 259,757

[22] Filed: May 1, 1981

[51] Int. Cl.³ ............................................. G01N 33/72
[52] U.S. Cl. ...................................... 436/66; 23/931; 422/56; 422/58
[58] Field of Search ...................... 23/230 B, 931, 932, 23/913; 422/56, 57, 58

[56] References Cited
U.S. PATENT DOCUMENTS

| | | | |
|---|---|---|---|
| 3,838,012 | 9/1974 | Higgens et al. | 422/56 X |
| 3,853,468 | 12/1974 | Haymond | 23/230 B |
| 3,986,834 | 10/1976 | Steinbrink, Jr. | 422/61 X |
| 3,996,006 | 12/1976 | Pagano | |
| 4,175,923 | 11/1979 | Friend | |
| 4,225,557 | 9/1980 | Hartl et al. | |

*Primary Examiner*—Arnold Turk
*Attorney, Agent, or Firm*—Joseph A. Marlino; Richard D. Foggio; Alan D. Lourie

[57] ABSTRACT

An improved specimen test slide having a front panel and a rear panel. The front panel has one or more openings. Sheet means carrying a test reagent underlie each of these openings for reception of a specimen. A hinged cover overlies the openings. The rear panel has flap means opposite said openings which is pivotable to expose the underside of the sheet to permit application of a developing solution. The underside of the sheet which faces the rear panel also has a control area positioned on a portion thereof at some distance from the portions of the sheet underlying the openings of the front panel. The control area contains positive and negative monitors.

5 Claims, 12 Drawing Figures

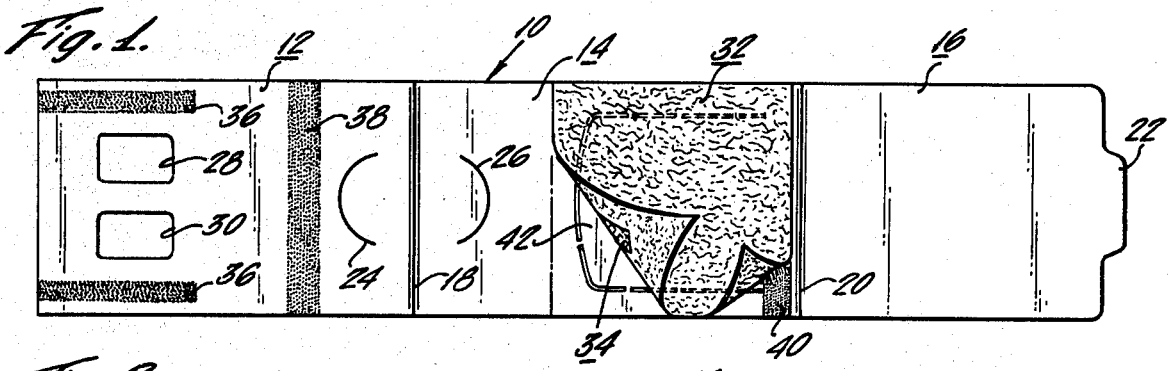
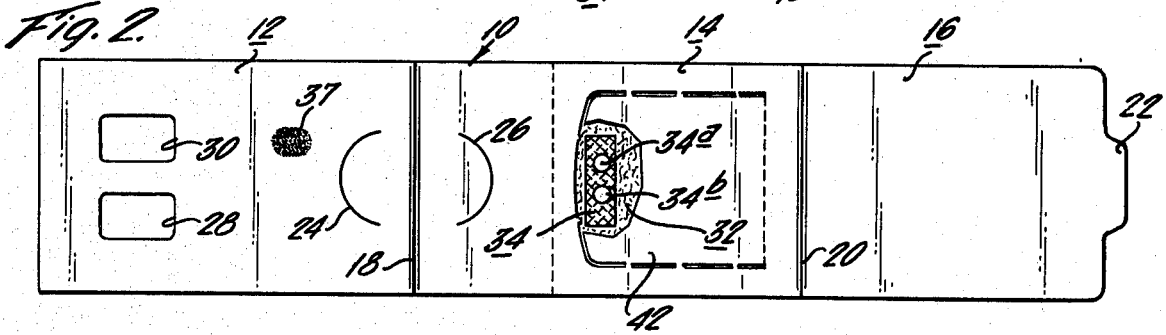
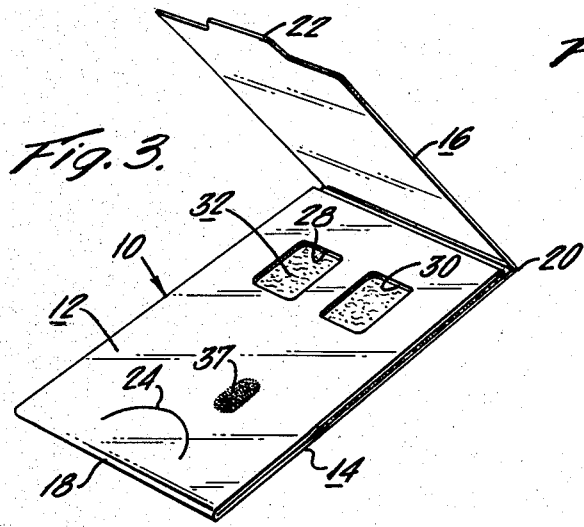
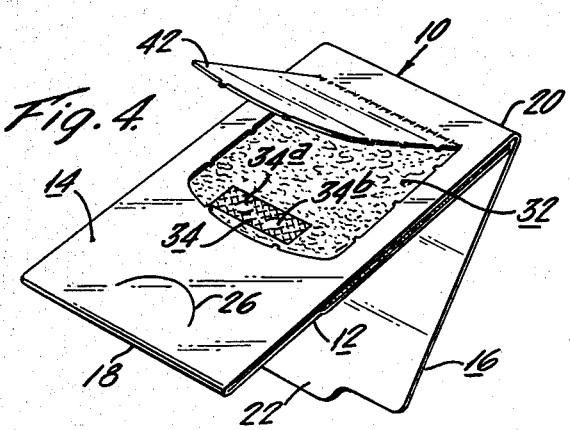
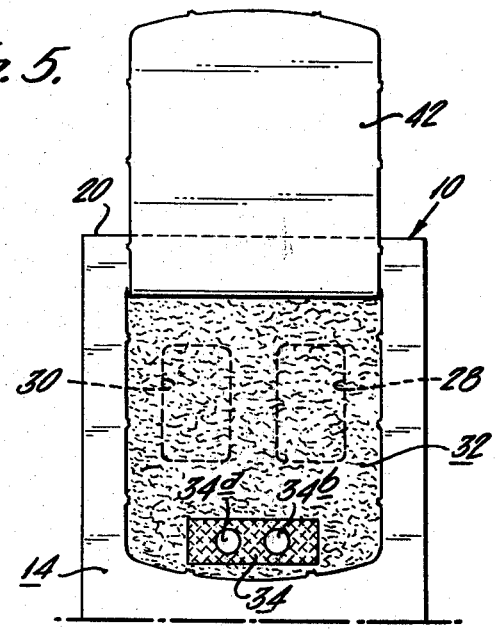
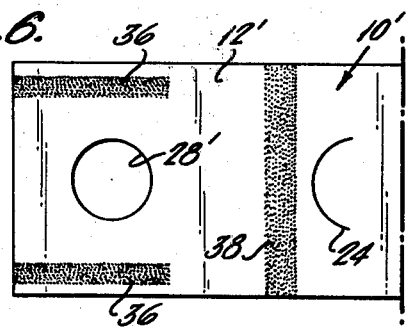

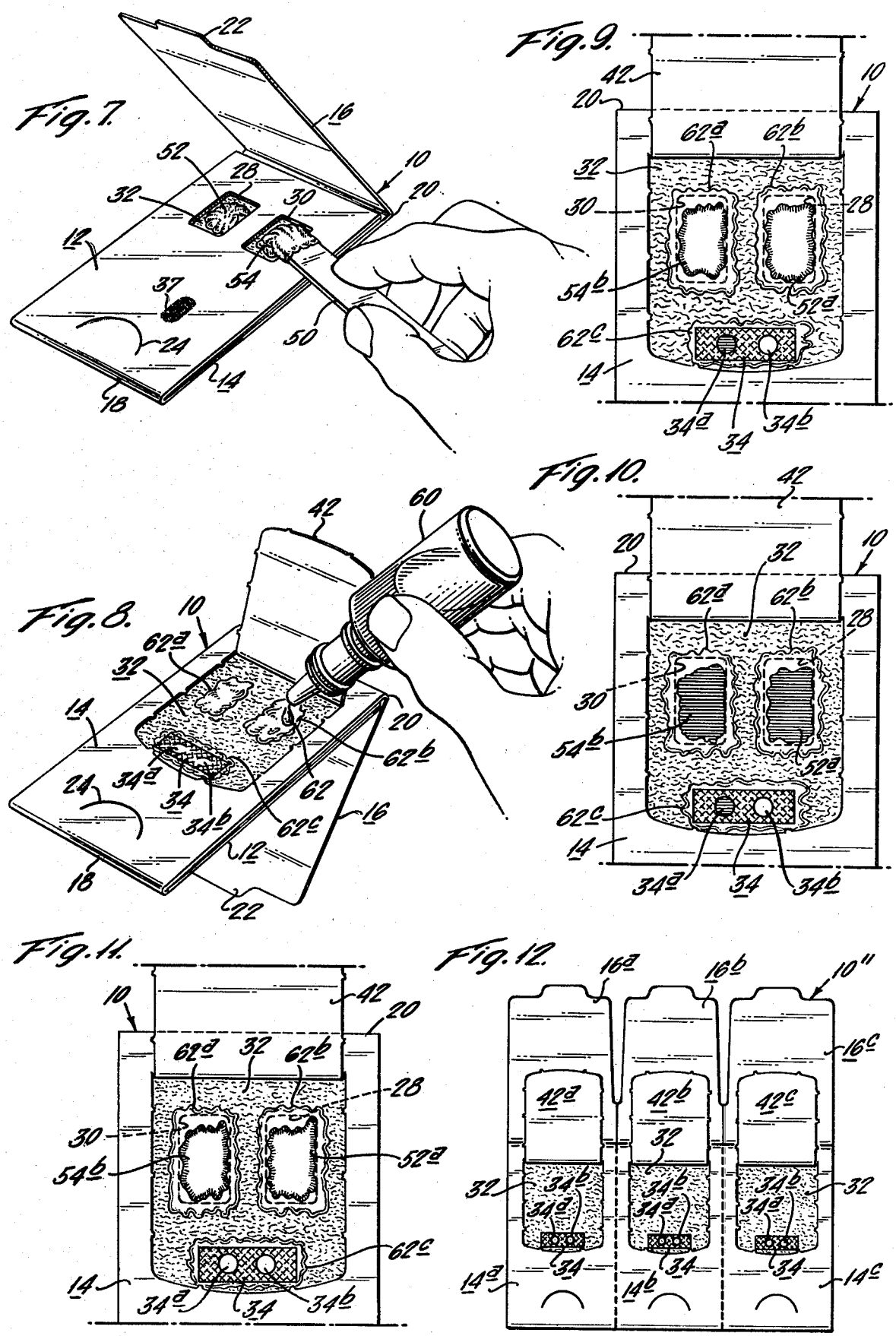

SPECIMEN TEST SLIDE AND METHOD FOR TESTING OCCULT BLOOD

Specimen test slides and procedures for detecting occult blood in fecal matter are well known. For example, U.S. Pat. No. 3,996,006 discloses slides having a specimen receiving sheet between a front panel and a rear panel with one or more openings in the front panel and an opening in the rear panel and pivotal covers to cover these openings. Typically, in the case of a test for occult blood in feces, the specimen receiving sheet is paper impregnated or printed with guaiac and a developing solution such as a peroxide solution is applied through the opening in the rear panel.

Briefly, the test procedure is as follows. A sample of fecal matter is smeared onto the guaiac paper through an opening of the front panel. The panel is then covered and the flap of the rear panel is opened. A developing solution such as hydrogen peroxide is applied to the guaiac paper via the corresponding opening in the rear panel. If blood is present in the fecal matter, the guaiac reaction will color the paper blue. The blue color is due to the hemoglobin catalyzed oxidation of the guaiac.

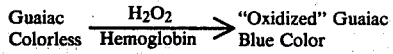

$$\text{Guaiac} \xrightarrow[\text{Hemoglobin}]{H_2O_2} \text{"Oxidized" Guaiac}$$
Colorless → Blue Color One of the disadvantages associated with this test is that false positive and false negative results can occur. For example, normally a patient will apply fecal specimens to the guaiac paper over a period of several days and deliver or mail the test slide to his physician or a laboratory for evaluation. While in the patient's home, or in transit, the slide is subjected to a variety of environmental conditions which may adversely affect the test performance.

Any condition such as exposure of the slide to heat or sunlight could cause loss of activity of either the guaiac or the hemoglobin present in the occult blood of the fecal specimen and could result in a false negative test. Alternatively, exposure of the slide to traces of metals such as copper or iron which are also guaiac catalysts could lead to false positive test. The test slide can be exposed to these conditions anytime between manufacture and testing procedure.

Previous attempts have been made to provide a control system for these slides. Presently available commercial slides provide catalytic substances to be applied to a portion of the slide immediately prior to developing the samples. These catalytic substances are supplied in bottles or tubes added to the test kit. This present control system therefore requires extra materials and more steps to perform the test. Most important, applying the control catalyst to the guaiac-based fecal specimen immediately prior to developing the sample does not eliminate the possibility of false results. If the slide were exposed to adverse conditions, as noted above, to degrade the hemoglobin in the feces, it naturally would have been done before the developing solution was added. Since the control substances are not added to the slide until it is time to be developed, the control substance was not subjected to the same adverse conditions as the fecal specimen and therefore a blue color will always appear in the control area of the slide.

It is therefore the object of this invention to provide a test slide and method for testing occult blood having a quality control check or performance monitor which gives an indication of the proper performance of the test system. It is still a further object of this invention to provide a simple, rapid, convenient, inexpensive and built-in control test which would monitor the test reagents from the date of manufacture to the date of development.

Briefly, this invention comprises an improved specimen test slide which includes a control area having built-in or on-slide positive and negative performance monitors. These comprise two small areas or spots printed on an isolated area of the guaiac test paper at some distance from the portions of the test paper underlying each of the openings in the front panel on the surface of the test paper facing the rear panel. In this manner the positive spot (monitor) is of such shape and size and placed in such a position relative to the stool sample(s) that there can be no confusion of its blue color with that of a positive stool sample. The positive monitor contains a printed spot of a blood component. The negative monitor positioned adjacent the positive monitor within the framed area is blank, an exposed area of the unmodified guaiac treated paper. Advantageously, the control area may be highlighted by framing the positive and negative monitors with a brightly colored inert border.

The slide of this invention is used in the same manner as the one described in the U.S. Pat. No. 3,996,006, except that the physician or lab technician who applies a drop of developing solution to the side of the test paper facing the rear panel at the locations opposite each of the openings in the front panel, where the fecal smears have been applied, also applies a drop of solution to the framed control area within the ink border. If the guaiac test paper and the developer are operating properly, the monitor printed with the blood component will turn blue while the monitor that has not been modified will remain white. Failure of the monitor printed with the blood component to turn blue would indicate that the blood-guaiac-developer reaction is not occurring, so that any negative result in the test would be suspect. Further, failure of the unmodified area to remain white would indicate that something in the test paper other than occult blood in the fecal smears was causing the guaiac-developer reaction to produce a blue color and that, therefore, any positive result in the test would be suspect.

A detailed description and better understanding of this invention can be had by referring to the accompanying drawings which show a preferred embodiment of the present invention.

FIG. 1 is a plan view of a blank, prior to folding, for preparing a slide in accordance with this invention.

FIG. 2 is a bottom plan view of the blank shown in FIG. 1.

FIG. 3 is a perspective view of the slide as shown from the front with the cover in an open position.

FIG. 4 is a perspective view of the slide as viewed from the rear, showing rear flap opened exposing the testing surface including the control area.

FIG. 5 is an enlarged fragmentary rear elevational view of the slide with the rear flap opened showing details of the test surface.

FIG. 6 is a fragmentary plan view of a blank showing a modified front panel.

FIG. 7 is a perspective view of the slide as shown from the front showing sample to be tested being applied.

FIG. 8 is a perspective view of the rear of the slide showing developing solution being applied to testing surface including control area.

FIG. 9 is an enlarged fragmentary rear elevational view showing a negative reaction.

FIG. 10 is an enlarged fragmentary rear elevational view showing a positive reaction.

FIG. 11 is an enlarged fragmentary rear elevational view showing a suspect test.

FIG. 12 shows additional modifications of FIG. 4. Referring to FIG. 1 and FIG. 2, a blank 10, formed for example from paper or cardboard, has a front panel 12, a rear panel 14, and a cover 16. The blank 10 is creased between panels 12 and 14 along the line indicated at 18 to facilitate folding. A crease along the line indicated at 20 between panel 14 and cover 16 facilitates the hinging of cover 16. Cover 16 has a tab 22 which is adapted to pass through circular slit 26 in panel 14 to lock the cover in a closed position.

Front panel 12 has a pair of adjacent openings 28 and 30. A sheet of absorbent paper 32 overlies openings 28 and 30. Adhesive strip 40 on the rear panel 14 adheres to one edge of sheet 32. Sheet 32 is impregnated or printed with a reagent such as guaiac. A portion of sheet 32 has a control area 34 having a positive monitor 34a and a negative monitor 34b. For the application of the developing solution, for example, a peroxide solution, rear panel 14 is provided with a flap 42 opposite openings 28 and 30. Tab 42 is moved away from sheet 32 to expose the testing area, sheet 32.

To form the completed slide as shown in FIG. 3, blank 10 is folded along crease line 18 to bring panels 12 and 14 together and hold them together principally by the adhesive strips 36. Cover 16 is now hinged about crease 20 and secured to panel 12 by a spot of adhesive 37, such as, for example, glue.

To use the slide, the patient separates cover 16 from panel 12 at the spot 37, opens the cover and applies with an applicator a thin smear of specimen from a portion of his stool on sheet 32 through opening 30, as viewed in FIG. 7. Another portion of the stool is similarly applied to sheet 32 through opening 28. The cover is then closed by locking tab 22 in slits 24 and 26. The patient returns the slide either to his physician or a laboratory. The physician or technician pulls flap 42 free of rear panel 14 and opens it outwardly. Through the opening thus made, the developing solution is applied to the test sheet 32 opposite each of the openings 28 and 30 to provide stained areas 62a and 62b. The developing solution is also added to control area 34 to cover positive and negative monitors 34a and 34b.

The test results are then observed. A negative result is displayed in FIG. 9. The positive monitor 34a, which contains hemin, develops a blue color as expected. The other moist areas 62a, 62b and negative monitor 34b are all colorless.

A positive result is disclosed in FIG. 10. The positive monitor once again turns blue together with the moist areas 62a and 62b. The negative monitor, being unmodified, remains colorless. FIG. 11 represents an invalid test. In this case failure of the positive monitor to turn blue would indicate the test is not performing properly. Positive monitor 34a should turn blue.

FIG. 6 shows a modified front panel containing only one opening and FIG. 12 shows an additional modification wherein six stool smears can be tested at the same time.

Since guaiac-based fecal occult blood tests are actually testing for the catalytic activity of hemoglobin in blood, the positive monitor should employ either hemoglobin or a catalyst which would react to adverse environmental conditions in a manner similar to hemoglobin. Preferably, the test slide of this invention employs hemin, a hemoglobin derived catalyst, as the catalyst in the positive monitor. The globin part of the hemoglobin molecule has little, if any, effect on the catalytic properties of the hemin it contains. Printable solutions of hemin are readily prepared and require approximately twenty-five times less hemin by weight than hemoglobin for the same catalytic activity. When printed on the guaiac treated paper the hemin spots have a stability comparable or greater than that of the slide.

The solution is prepared by dissolving approximately 10 mg./ml. of crystalline hemin in a combination of water, ammonium hydroxide and isopropanol. The hemin solution is then printed as registered spots on standard rolls of guaiac paper.

If desired, a second stage of printing would register a bright color frame, such as orange, around the monitors. The color intensity of the orange may be adjusted by proper dilution of the ink.

The above embodiments are illustrative and are not intended to be limiting.

What is claimed is:

1. In an occult blood specimen test slide having a front panel, a rear panel, said front panel having one or more openings, sheet means carrying a test reagent between the front and rear panels underlying each of said openings, a hinged cover adapted to overlie a portion of the front panel and said openings and flap means in the rear panel opposite said openings and pivotable to expose the underside of the sheet, the improvement comprising: an area positioned on a portion of the sheet means facing the rear panel and isolated from the openings in the front panel, said area including a positive and negative monitor, said positive and negative monitors including the test reagent and said positive monitor additionally including a compound that reacts to environmental conditions in a manner similar to hemoglobin.

2. The slide of claim 1 in which the compound in the positive monitor is a blood component and the test reagent is guaiac.

3. The slide of claim 2 in which the blood component is hemin.

4. The slide of claim 2 in which the positive and negative monitors are framed by a brightly colored inert border.

5. In a method for determining the presence of occult blood on a specimen test slide having a guaiac treated specimen receiving sheet between a front panel and a rear panel with openings in the front and rear panels and pivotable covers to cover said openings which consists of smearing fecal matter onto the guaiac sheet through an opening of the front panel and applying a developing solution to the guaiac sheet at the corresponding opening in the rear panel the improvement which comprises further applying the developing solution to an area positioned on a portion of the sheet facing the rear panel and isolated from the openings in the front panel, said area including a positive and negative monitor, said positive and negative monitors including the guaic and said positive monitor additionally including a compound that reacts to environmental conditions in a manner similar to hemoglobin.

* * * * *